(12) United States Patent
Agarwala et al.

(10) Patent No.: US 7,399,490 B2
(45) Date of Patent: Jul. 15, 2008

(54) COMPOSITIONS CONTAINING A NOPAL CACTUS ISOLATE AND METHOD FOR MAKING SAME

(75) Inventors: Om P. Agarwala, Las Vegas, NV (US); Chandrakala Agarwala, Las Vegas, NV (US); Teri Amato, Bayside, NY (US)

(73) Assignee: Lean For Life, Inc., Mineola, NY (US)

( * ) Notice: Subject to any disclaimer, the term of this patent is extended or adjusted under 35 U.S.C. 154(b) by 527 days.

(21) Appl. No.: 10/847,217

(22) Filed: May 17, 2004

(65) Prior Publication Data
US 2005/0255215 A1 Nov. 17, 2005

(51) Int. Cl.
*A61K 36/00* (2006.01)
*A61K 9/00* (2006.01)

(52) U.S. Cl. ...................... 424/725; 424/400

(58) Field of Classification Search ................ 424/725
See application file for complete search history.

(56) References Cited

U.S. PATENT DOCUMENTS

| | | | |
|---|---|---|---|
| RE2,912 E | 4/1868 | Lege | |
| 2,082,952 A | 6/1937 | Gruwell et al. | |
| 4,824,672 A | 4/1989 | Day et al. | |
| 5,545,414 A | 8/1996 | Behr et al. | |
| 5,738,887 A | 4/1998 | Wu | |
| 5,747,462 A | 5/1998 | Fuentes | |
| 6,036,984 A | 3/2000 | Sartorio et al. | |
| 6,210,738 B1 | 4/2001 | Chen | |
| 6,238,672 B1 | 5/2001 | Chen | |
| 6,365,198 B1 | 4/2002 | Niazl | |
| 6,576,286 B1 | 6/2003 | Chen | |
| 6,641,847 B1 | 11/2003 | Nawar | |
| 6,669,952 B2 | 12/2003 | Waggle et al. | |
| 6,737,086 B2 * | 5/2004 | Gutierrez et al. ............ | 424/767 |
| 6,749,883 B2 * | 6/2004 | Kim ........................... | 426/615 |
| 2001/0021694 A1 | 9/2001 | Portman | |
| 2002/0182304 A1 | 12/2002 | Kim | |
| 2003/0008058 A1 | 1/2003 | Ariga et al. | |

FOREIGN PATENT DOCUMENTS

| | | | |
|---|---|---|---|
| ES | 2143439 | | 5/2000 |
| JP | DW ACC 1998-220068 | * | 6/1997 |
| WO | WO 02/082930 A1 | | 10/2002 |

OTHER PUBLICATIONS

F.F. Feitosa Teles, (Amino and Organic Acids of the Prickly Pear (*Opuntia ficus Indica*), J.Sci.Food Agric. 1984,35, 421-425.*
Ahmad, et al. "Antiviral properties of extract of *Opuntia streptacantha*," *Antiviral Res*, pp. 75-85, 30:2-3 (1996) (Abstract).
Arnholdt-Schmitt, et al. "Genome Characterization of *Opuntia ficus-indica*: A Simple and Efficient Micromethod," *J. Pacd*, pp. 57-65, (2001).
Cardenas Medellin, et al. "Effect of raw and cooked nopal (*Opuntia ficus indica*) ingestion on growth and profile of total cholesterol, lipoproteins, and blood glucose in rats," *Arch Latinoam Nutr.*, pp. 316-323, 48:4 (1998) (Abstract).
D'Eeckenbrugge, et al., "Fruits from America," *CIRAD-FLHOR/IPGRI Project for Neotropical Fruits*, (2000).
Terrazas, et al., "Prickly Pear (*Opuntia ficus-indica*) Peels as a New Desert Fiber: Preparation and Pertial Chacaterization," Annual Meeting and Food Expo-Anaheim, CA (2002) (Abstract).
Dok-Go, et al., "Neuroprotective effects of antioxidative flavonoids, quercetin, dihydroquercetin and quercetin 3-methyl ether, isolated from *Opuntia ficus-indica* var. saboten." *Brain Res.* pp. 130-136, 7:965(1-2), (2003) (Abstract).
Fernandez, et al., "Prickly pear (*Opuntia* sp.) pectin reverses low density lipoprotein receptor suppression induced by a hypercholesterolemic diet in guinea pigs." *J Nutr.* pp. 2330-2340, 122:12, (1992) (Abstract).
Frati Munari, et al. "Evaluation of nopal capsules in diabetes mellitus," *Gac Med Mex.*, pp. 431-436, 128:4 (1992) (Abstract).
Frati, et al. "Influence of nopal intake upon fasting glycemia in type II diabetics and healthy subjects," *Arch Invest Med (Mex)*, pp. 51-56, 22:1 (1991) (Abstract).
Frati, et al. "The effect of two sequential doses of *Opuntia streptacantha* upon glycemia," *Arch Invest Med (Mex)*, pp. 333-336, 22:3-4 (1991) (Abstract).
Frati-Munari, et al. "Activity of *Opuntia streptacantha* in healthy individuals with induced hyperglycemia," *Arch Invest Med (Mex)*, pp. 99-102, 21:2 (1990) (Abstract).
Frati-Munari, et al. "Duration of the hypoglycemic action of *Opuntia streptacantha* Lem," *Arch Invest Med (Mex)*, pp. 297-300, 20:4 (1989) (Abstract).
Frati-Munari, et al. "Effect of a dehydrated extract of nopal (*Opuntia ficus indica* Mill.) on blood glucose," *Arch Invest Med (Mex)*, pp. 211-216, 20:3 (1989) (Abstract).
Frati-Munari, et al. "Hypoglycemic action of different doses of nopal (*Opuntia streptacantha lemaire*) in patients with type II diabetes mellitus," *Arch Invest Med (Mex)*, pp. 197-201, 20:2 (1989) (Abstract).
Frati-Munari, et al. "Hypoglycemic action of *Opuntia streptacantha lemaire*: study using raw extracts," *Arch Invest Med (Mex)*, pp. 321-325, 20:4 (1989) (Abstract).
Frati-Munari, et al. "Hypoglycemic effect of *Opuntia streptacantha lemaire* in NIDDM," *Diabetes Care*, pp. 63-66, 11:1 (1988) (Abstract).
Ibanez-Camacho, et al. "Hypoglycemic effect of *Opuntia* cactus," *Arch Invest Med (Mex)*, pp. 223-230, 10:4 (1979) (Abstract).
Laurenz, et al. "Hypoglycaemic effect of *Opuntia lindheimeri* Englem in a diabetic pig model," *Phytother Res.*, pp. 26-29, 17:1 (2003) (Abstract).
Lee, et al. "Constituents of the stems and fruits of *Opuntia ficus-indica* var. saboten," *Arch Pharm Res.*, pp. 1018-1023, 26:12 (2003) (Abstract).

(Continued)

Primary Examiner—Christopher R. Tate
Assistant Examiner—Randall Winston
(74) Attorney, Agent, or Firm—Hoffmann & Baron, LLP

(57) ABSTRACT

Compositions and methods of making compositions containing nopal cactus isolates derived from the juice and/or soluble solid fractions of nopal pads. In another aspect, the invention relates to compositions for making coffee, coffee compositions and methods of making such compositions, which contain nopal cactus isolates.

15 Claims, 1 Drawing Sheet

OTHER PUBLICATIONS

Lee, et al. "Effects of *Opuntia ficus-indica* var. Saboten stem on gastric damages in rates," *Arch Pharm Res.*, pp. 67-70, 25:1 (2002) (Abstract).

Meckes-Lozoya, et al. "Hypoglucaemic activity of *Opuntia streptacantha* throughout its annual cycle," *Am J Chin Med,* pp. 221-224, 17:3-4 (1989) (Abstract).

Park, et al. "An anti-inflammatory principle from cactus," *Fitoterapia,* pp. 288-290, 72:3 (2001) (Abstract).

Park, et al. "Studies on the pharmacological action of cactus: identification of its anti-inflammatory effect," *Arch Pharm Res.*, pp. 30-34, 21:1 (1998) (Abstract).

Park, et al. "Wound healing activity of *Opuntia ficus-indica*," *Fitoterapia,* pp. 165-167, 72:2 (2001) (Abstract).

Shapiro, et al. "Natural products used for diabetes," *J Am Pharm Assoc (Wash)*, pp. 217-226, 42:2 (2002) (Abstract).

Tuomilehto, et al. "Coffee consumption and risk of type 2 diabetes mellitus among middle-aged Finnish men and women," *JAMA,* pp. 1213-1219, 291 (2004).

VitaliTrim—http://www.freevitalitrim.com (available on the internet at least as early as Jan. 29, 2004).

Alarcon-Aguilar, et al. "Hypoglycemic Activity of Two Polysaccharides Isolated From *Opuntia ficus-indica* and *O. streptacantha*," *Proc. West Pharmacol. Soc.,* pp. 139-142, 46 (2003)(No Abstract).

Frati, Alberto, "Medical Implications of Prickly Pear Cactus," *Instituto Mexicano del Seguro Social,* http://myweb.ecomplanet.com/BADR2752/mycustompage0013.htm (available on the internet at least as early as Mar. 31, 2004).

* cited by examiner

COMPOSITIONS CONTAINING A NOPAL CACTUS ISOLATE AND METHOD FOR MAKING SAME

BACKGROUND OF THE INVENTION

The present invention relates to dietary supplements and compositions containing nopal cactus isolates derived from the juice and/or soluble solid fractions of nopal pads and methods of preparing the supplements and compositions. The invention also specifically relates to compositions for making coffee, coffee compositions and methods for making such compositions, which contain the nopal cactus isolates.

In developed countries around the world, there is a tremendous interest in personal fitness and wellness. At the same time there is a disturbing trend that people, including adults and children are becoming overweight. By overweight, it is meant that the subject has exceeded acceptable weight range and percent body fat generally considered as healthy determined by factors including, but not necessarily limited to age, height, sex, and body type. For example, over 50% of the human population in the United States is considered overweight, approximately 20% being obese. Obesity produces a wide range of health concerns including sleep apnea, orthopedic complications, arterial sclerosis, diabetes and heart disease. All these undesirable conditions contribute in development of an unsatisfactory quality of life and in some cases premature death.

Many studies have been conducted to identify the factors that contribute to being overweight. The main factors include high caloric density in foods, large portion sizes, diets that are rich in fat, decreasing amounts of exercise, high availability of food, increased numbers of eating occasions, low knowledge of actual foods and portions eaten by the consumer, lack of information on energy expenditure through normal daily activities and exercise, and eating stimulated by stress, hormonal shifts during the menstrual cycle for women, and hunger. A number of approaches to control the caloric balance including consumable products have been developed with mixed success. In the United States, over the counter weight loss products are sold to help consumers reduce their weight or maintain current weight. These products are grouped into over the counter diet aids and meal replacements. The over the counter diet aids include appetite suppressants, like Dexatrim® and Acutrim®, which both use phenylpropranolamine (PPA) as the appetite suppressant. This appetite suppressant can even be released over time to help control hunger for longer periods of time for the consumer. In addition, there are dietary supplements, like Metabolife 356®, which help people with their diets while providing energy. Consumers use these products up to 3 times a day to help control hunger and increase energy. However, many supplements have been shown to have potentially dangerous side effects, such as increased risk of hemorrhagic stroke from PPA containing supplements.

There are also prescription drugs that can help consumers to lose weight that fall into the anti-obesity drug class. These drugs are used to decrease appetite or increase the feeling of being full by possibly increasing levels of serotonin or catecholamine—two brain chemicals that effect mood and appetite. Examples of products in this group include Fastin® from Smith-Kline-Beechan which uses phentermine hydrochloride, Meridia® from Knoll-BASF Pharma which uses sibutramine and Pondimin® from Wyeth Ayerst which uses phenfluramine hydrochloride and Redux® from Wyeth Ayerst which uses dexfenfluramine. All of these products must be obtained through a physician by use of a prescription. Again, such products typically include potent stimulants that can have potentially dangerous side effects, such as increased blood pressure and, in some cases, damage to a patient's pulmonary system. Some prescription diet drugs can also be highly addictive resulting in the patient becoming physically and psychologically dependent on the medication.

There are also commercial weight loss programs available through programs like Weight Watchers®, Jenny Craig®, and hospital supervised programs that are designed to help consumers track energy intake and energy output through a variety of techniques and devices. While many of the technologies mentioned above can be useful in losing weight, the problem is keeping the weight off. Short term diets can be unhealthy because it causes the body to adopt a starvation mode, lowers the metabolism and lowers the ability to burn fat. Often people "yo-yo", that is, lose large amounts of weight only to gain it back once they get off the weight loss program they were on. This so-called "yo-yo" effect can damage a person's health by zapping energy and destroying their metabolism, leading to binge eating, craving and feelings of deprivation.

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and dyslipidemia, including hyperinsulinema due to insulin resistance. Several of these factors, particularly dyslipidemia and chronically elevated serum insulin, contribute to the development of atherosclerosis, a primary cause of vascular and heart disease.

Insulin resistance is a common metabolic disorder in modern Western society, predisposed to largely as a result of factors in modern Western society living. Poor insulin activity and chronically elevated blood insulin levels are associated with a number of serious diseases. Among these, hypertension, obesity, ischaemic heart disease, dyslipidemia and non-insulin-dependent diabetes mellitus (NIDDM) are major diseases in which insulin resistance has a clearly demonstrated relationship with the etiology and clinical course of the disease.

Nopal cactus fruit and pads of the *opuntia* cactus genus have been a food staple of the natives of the Americas for thousands of years. Virtually every fruit and vegetable store in Mexico, central and South America sell the fruit and young tender nopal pads. The fruit is also known as prickly pear fruit. The fleshy leaves (or pads) of the nopal cactus are large, circular, paddle-like members that typically grow to be 7 to 10 inches in length, 4 to 5 inches in width and 0.5 inches thick.

It has been reported that the fruit and pads from the *opuntia* genus of cactus, which are rich in vitamins and minerals, act as natural fat blockers, can reduce serum low-density lipoprotein-cholesterol (LDL), and can reduce blood glucose levels in hyperglycemic individuals by increasing insulin sensitivity. However, in order to realize the full health benefits of the fruit and pads of the prickly pear cactus, a person would need to consume a significant amount (e.g., 300-500 g of cooked nopal pads per day) of the fruit or pads on a regular basis. Moreover, the fruit and pads of the prickly pear cactus are not available in all areas or during all seasons.

Thus, there is a need for new dietary or nutritional food products containing natural ingredients which are effective for lowering cholesterol, stabilizing blood glucose and insulin levels and promoting healthy weight management, which can reduce the risks of coronary heart disease and diabetes without the side effects and disadvantages of known supplements or products, including the disadvantages described above. Moreover, new methods and compositions utilizing concentrated nopal cactus components which are capable of providing significant lowering of LDL in the blood to significantly reduce the risk of atherosclerosis and coronary heart disease remain desirable.

SUMMARY OF THE INVENTION

The present invention is directed to dietary supplements and compositions containing nopal cactus isolates and methods of preparing the supplements and compositions. The isolates are derived from the juice and/or soluble solid fractions of nopal pads of the *opuntia* genus, preferably the *opuntia ficus indica* and/or *opuntia streptacantha lemaire* variety. The invention also specifically relates to compositions for making coffee, coffee compositions and methods for making such compositions, which contain the nopal cactus isolates.

In one aspect, the invention relates to a composition for making coffee which includes a nopal cactus isolate and roasted ground coffee beans. The isolate is preferably derived from the juice and/or soluble solid fractions of nopal pads of the *opuntia* genus. Preferably, the nopal pads are from the *opuntia ficus indicia* and/or *opuntia streptacantha lemaire* variety.

The nopal cactus isolate can be freeze-dried. Preferably, the freeze-dried isolate is present in an amount to enhance weight reduction and/or reduce cholesterol as a result of consuming the coffee made from the composition.

It is preferred that the nopal pads are young nopal pads harvested prior to flowering of the cactus plant. It is also preferred that the nopal pads are roasted in a controlled manner to enhance the flavor of the isolate. More specifically, the isolate can have a flavor that is compatible with brewed coffee.

The composition can be in a form suitable for making coffee by a method selected from the group consisting of drip, percolation, press, espresso, latte, instant coffee and flow-through bag. Preferably, the coffee made by the present composition is intended to be served hot.

In another aspect, the invention is directed to a method of making a coffee composition which includes blending a freeze-dried nopal isolate powder with ground coffee beans.

In a preferred embodiment, the isolate powder is prepared by (i) roasting nopal cactus pads of *opuntia ficus indica* and/or *opuntia streptacantha lemaire* variety to enhance the flavor of coffee prepared from the coffee composition; (ii) substantially separating insoluble pulp from soluble solids and nopal pad juice; (iii) concentrating the juice and soluble solids; and (iv) freeze-drying the concentrate to form a powder.

The nopal cactus pads are typically (i) cleaned and de-thorned before roasting and (ii) ground after roasting to release the nopal pad juice and soluble solids. The nopal cactus pads can be cleaned using a water and chlorine solution to remove organic debris. In one embodiment, the pads are soaked in a solution having a pH of about 7.5 for about 10 minutes, e.g., in a sodium bicarbonate solution, prior to roasting. The roasting step preferably includes roasting the pads to achieve about a level 2 roast, on the coffee roasting scale. The grinding of the pads is preferably accomplished by using a hammer mill grinder.

In one embodiment, the ground nopal pads are heated sufficiently to substantially inactivate cellulase enzymes naturally present in the pads prior to separating insoluble pulp from the juice and soluble solid fractions. Inactivating cellulose enzyme stabilizes the nutrients present in the nopal filet and prevents it from breaking down. Preferably, the heating is accomplished by immediately steam heating the ground nopal pads to at least about 160° F. More preferably, the ground nopal is steam heated immediately after grinding. Most preferably, the heating is accomplished by simultaneously steam heating and grinding the nopal pads.

The separating step is preferably accomplished by filtering the insoluble pulp out of the juice and soluble solid fractions.

In an embodiment of the invention, the method includes pasteurizing the juice and soluble solids fractions. Preferably, the pasteurization is accomplished by flash pasteurizing the juice and soluble solid fractions, e.g., at a temperature of at least about 192° F. for about 10 seconds. The pasteurized juice/soluble solids can then be concentrated by concentrating the pasteurized juice and soluble solid fractions to a concentrate suitable for freeze-drying. The concentrating step is preferably accomplished by using reverse osmosis to concentrate the juice to about a 12% solids concentration.

In another embodiment, the method includes adjusting the pH of the concentrated juice and soluble solids to substantially match the pH of coffee. Preferably, the concentrate is adjusted to a pH of about 5.0. The method can also include subjecting the adjusted concentrate to a second pasteurization step. Preferably, the second pasteurization step is carried out by flash pasteurizing the concentrate, e.g., at a temperature of at least about 192° F. for about 10 seconds.

In one embodiment, the method also includes filtering the juice and soluble solid fractions to provide a substantially clear liquid. The filtering step is preferably accomplished by recycling the juice through a diatomaceous earth filter. The substantially clear liquid is preferably pasteurized and concentrated to a concentrate suitable for freeze-drying. The pH of the substantially clear liquid is preferably adjusted to substantially match the pH of coffee.

It is also contemplated that the method includes adding at least one preservative to the nopal juice and/or soluble solid fractions prior to freeze-drying.

The concentrated juice and soluble solids are preferably freeze-dried to form a powder that has a moisture content of less than about 7%. The freeze-dried powder can be ground to a selected size prior to blending with the ground coffee beans. Preferably, the freeze-dried nopal powder is ground to a granule size of about 100 mesh.

The final blend preferably contains about 2 to about 30 wt %, more preferably, about 5 to about 25 wt % and, most preferably, about 5 wt % of the ground freeze-dried nopal powder.

In another aspect, the invention is more generally directed to a dietary supplement, which includes a nopal cactus isolate derived from the juice and/or soluble solid fractions of nopal pads of the *opuntia ficus indica* and/or *opuntia streptacantha lemaire* variety.

In one embodiment, the supplement includes a therapeutically effective amount of the isolate to reduce or maintain weight, or an effective amount to reduce cholesterol.

The isolate is preferably derived from young nopal pads harvested prior to flowering of the plant. Preferably, the nopal pads are roasted to enhance the flavor of the isolate.

In one embodiment, the supplement is in liquid form. Preferably, the supplement is in a form selected from the group consisting of a juice, coffee and tea.

In yet another aspect, the invention is directed to a method for making a dietary supplement, which includes roasting nopal cactus pads of the *opuntia* genus; grinding the roasted pads; substantially separating juice and soluble solid fractions from insoluble fractions of the ground and roasted pads; and freeze-drying the juice and soluble fractions to form a powder. Preferably, the nopal pads are of a variety selected from the group consisting of *opuntia ficus indica, opuntia streptacantha lemaire* and combinations thereof.

The method can include blending the powder with ground roasted coffee beans to provide a composition suitable for brewing coffee. In such a case, the roasting step is preformed under conditions to develop a taste that will be compatible with brewed coffee.

The method can also include, prior to freeze-drying, the steps of heating the ground nopal pads to inactivate the cellulase enzyme naturally present in fresh nopal pads; filtering out the insoluble pulp from the nopal pad juice and soluble solid fractions; filtering the nopal pad juice and soluble solid fractions until the juice becomes clear; flash pasteurizing the clear juice; concentrating the pasteurized juice to a concentration suitable for freeze-drying; adjusting the pH of the concentrate; and subjecting the concentrate to a second flash pasteurization step. Preferably, the pH is adjusted to about 5.0. The method can also include adding at least one preservative to the juice.

In yet another aspect, the invention is directed towards a method for lowering cholesterol, stabilizing blood glucose and insulin levels and/or promoting healthy weight management. The method includes administering coffee made from the composition for making coffee which includes a nopal cactus isolate, as described above, in a therapeutically effective amount and at a frequency sufficient to lower cholesterol, stabilize blood glucose and insulin levels and/or promote healthy weight management.

In another aspect, the invention is directed to an item of manufacture which includes a container containing a coffee composition, that includes a blend of ground roasted coffee and a nopal cactus isolate, wherein the container is associated with printed labeling advising of the attributes or benefits of the coffee composition. The attributes or benefits can include lowering cholesterol, stabilizing blood glucose and insulin levels or reducing (or maintaining) weight by consuming coffee made from the coffee composition.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Figure 1:
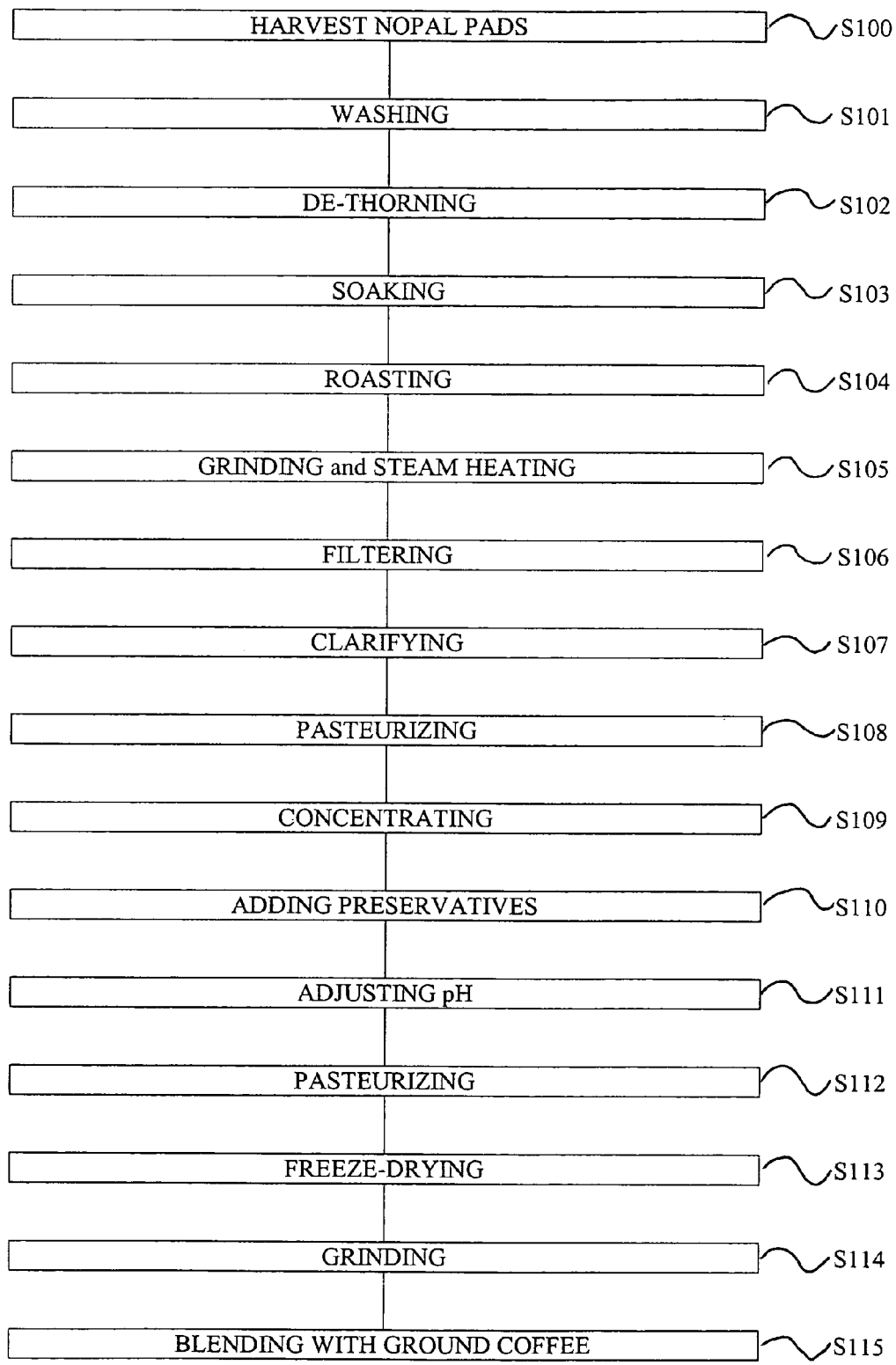
FIG. 1 is a flowchart showing a process for preparing a coffee blend containing isolate granules from nopal cactus pads according to a preferred embodiment of the present invention.

The present invention is directed to dietary supplements and compositions containing nopal cactus isolates, methods of making such supplements and methods for improving health by consuming such supplements. The isolates are preferably derived from the juice and/or soluble solid fractions of nopal pads of the *opuntia ficus indica* and/or *opuntia streptacantha lemaire* variety.

The nopal cactus isolates according to the invention maximize the effects of lowering cholesterol, stabilizing blood glucose and insulin levels and promoting healthy weight management, which can reduce the risks of coronary heart disease and diabetes without the side effects and disadvantages of other supplements or products currently being used. While not being bound by theory it is believed that the nopal cactus isolates of the present invention maximize the concentration and availability of phytonutrients which are contained in the nopal pad juice and soluble solid fractions and which are effective for lowering cholesterol, stabilizing blood glucose and insulin levels and promoting healthy weight management. It is also believed that by isolating the juice and soluble solid fractions from the insoluble fiber and solid materials, the availability and uptake of the desired phytonutrients is improved.

The nopal cactus isolates are also prepared in such a way as to enhance the flavor of the nopal pad juice and resulting isolate, and to achieve a particle size and density which is compatible with ground coffee. This results in a coffee product having superior flavor, while maximizing the delivery and uptake of the phytonutrients naturally found in the nopal pad juice and soluble solid fractions.

Consuming coffee which contains the nopal pad isolates is a convenient and effective way to obtain the health benefits of the nopal isolates. It is also believed that the nopal isolates and coffee work together synergistically to increase metabolism, reduce obesity and control weight, while at the same time lowering cholesterol and blood glucose and insulin levels.

In one aspect, the invention relates to a composition for making coffee which includes a nopal cactus isolate, derived from the juice and/or soluble solid fractions of nopal pads of the *opuntia ficus indica* variety, and roasted ground coffee beans.

The nopal cactus isolate can be freeze-dried. Preferably, the freeze-dried isolate is present in an amount to enhance weight reduction and/or reduce cholesterol as a result of consuming the coffee made from the composition.

It is preferred that the nopal pads are young nopal pads harvested prior to flowering of the cactus plant. It is also preferred that the nopal pads are roasted in a controlled manner to enhance the flavor of the isolate. More specifically, the isolate can have a flavor that is compatible with brewed coffee.

The composition can be in a form suitable for making coffee by a method selected from the group consisting of drip, percolation, press, espresso, latte, instant coffee and flow-through bag. Preferably, the coffee made by the present composition is intended to be served hot. Thus, it is also contemplated that the composition can be brewed into coffee and then the brewed coffee can be freeze-dried or otherwise formed into a reconstitutable powder that, when reconstituted with hot water, provides a nutritionally superior product to simple brewed coffee, and that possesses the health benefits of the nopal pad isolate.

It is also contemplated that the coffee can contain other ingredients to provide additional health benefits or to improve the drinking experience. Preferably, the ingredients that provide additional health benefits are natural health promoting ingredients, such as, for example, Bitter Orange, Gracinia Cambogia or Kola Nut Extract.

Ingredients that improve the drinking experience can include sweeteners, whitening agents or flavorants. Preferred flavorants include spices such as cinnamon, mint, peppermint, cardamom, ginger and nut flavors.

While not being bound by theory, it is postulated that the nopal pad isolates in combination with coffee according to the present invention allows the phytonutrients of the nopal pad isolates to rapidly disperse and thereby be more available for their cholesterol lowering and blood glucose lowering effects. Accordingly, while it is preferred that the coffee is regular caffeine containing coffee, it is also contemplated that the coffee blend according to the invention can include de-caffeinated coffee, reduced caffeine coffee or a combination (or mixture) of regular caffeinated and decaffeinate coffee.

In another aspect, the invention is directed to a method of making a coffee composition which includes blending a freeze-dried nopal isolate powder with ground coffee beans. It is also contemplated that the nopal isolate powder can be prepared by other methods, such as, for example, spray drying.

In a preferred embodiment, the isolate powder is prepared by (i) roasting nopal cactus pads of *opuntia ficus indica* and/or *opuntia streptacantha lemaire* variety to enhance the flavor of coffee prepared from the coffee composition; (ii) substantially separating insoluble pulp from soluble solids and nopal pad juice; (iii) concentrating the juice and soluble solids; and (iv) freeze-drying the concentrate to form a powder.

The nopal pads, preferably the new petal growth, referred to as the "nopalito" from the *opuntia ficus indica* and/or *opuntia streptacantha lemaire* species of cactus, are selectively harvested, typically by cutting each leaf (or pad) manually.

The nopal cactus pads are then typically (i) cleaned and de-thomed before roasting and (ii) ground after roasting to release the nopal pad juice and soluble solids. The harvested nopal pads are first cleaned, e.g., by washing in a water and chlorine mixture to remove organic debris. The nopal pads are then de-thorned, e.g., by manually removing the thorns. In a preferred embodiment, the de-thorned pads are soaked in a basic solution, preferably about at a pH of about 7.1 to about 8.5, and more preferably about 7.5, for about 10 minutes prior to roasting, for example, in a sodium bicarbonate solution. It is believed that this soaking step maximizes or at least improves, the extraction of the desirable phytonutrients.

The roasting step preferably includes roasting the cleaned and de-thomed pads to achieve about a level 2 roast, on the coffee roasting scale. The coffee roasting scale is well known to those skilled in the art of coffee bean roasting and is based on the color of the roasted beans. The roasted beans are rated on a scale from 1 to 5, with 1 being the lightest roast and 5 being a very dark roast. The roasting step can be carried out by roasting the nopal pads at a temperature of about 250-400° F. for about 3-5 minutes with each side being roasted for approximately 1.5-2.5 minutes. An Excelsior Drum Roaster made by Probat was found to be acceptable for roasting the nopal pads.

The roasted pads can be ground by any conventional means which sufficiently disrupts or dissociates the juice and soluble solid fractions from the insoluble solid or fiber fractions of the pads. The grinding of the pads is preferably accomplished by using a hammer mill grinder.

In one embodiment, the ground nopal pads are heated sufficiently to substantially inactivate cellulase enzymes naturally present in the pads prior to separating insoluble pulp from the juice and soluble solid fractions. Preferably, the heating is accomplished by steam heating the ground nopal pads to at least about 140° F., more preferably at least about 150° F. and most preferably at least about 160° F. The heating step is preferably carried out immediately upon grinding the pads. Preferably, a hammer mill grinder equipped with steam nozzles, such as the Ritz Disintegrator, Model RP12, is used to immediately heat the ground nopal, i.e., steaming simultaneously while grinding. In addition to inactivating cellulose enzymes, heating with steam reduces the viscosity of the nopal juice. It is believed that this simultaneous steaming while grinding preserves the pharmacologically active components of the nopal for maximum efficaciousness and prevents degradation of such components. It is also believed that immediate steam heating after grinding (or simultaneous with grinding) also pasteurizes the nopal material, preventing breakdown of nutrients by microorganisms and preserving the efficaciousness of the material during processing.

The separating step is preferably accomplished by filtering the insoluble pulp out of the juice and soluble solid fractions. The filtering step can be accomplish by filtering the juice and soluble solid fractions, using a finisher of a type well known in the food processing industry. For example, a Brown Model No. 3900 or 2503 screw type finisher is suitable for separating out the insoluble solid fractions from the juice and solid soluble fractions.

In an embodiment of the invention, the method includes pasteurizing the juice and soluble solid fractions. The isolated juice/soluble solid fractions can be pasteurized using known methods to stabilize and significantly reduce the amount of any micro-organisms present. Preferably, the pasteurization is accomplished by flash pasteurizing the juice and soluble solid fractions at a temperature of at least about 170° F., more preferably at least about 180° F. and most preferably at least about 192° F. for about 10 seconds.

The pasteurized juice/soluble solids can then be concentrated by concentrating the pasteurized juice and soluble solid fractions to a concentrate suitable for freeze-drying. The concentrating step is preferably accomplished by removing water to provide a concentrate having at least about 8 wt %, more preferably at least about 10 wt % and most preferably at least about 12 wt % solids concentration. Preferably, the concentrating step is carried out at room temperature by using an Osmonics reverse osmosis method to achieve about a 12 to 15 wt % solids concentration. It is believed that concentrating the juice/soluble solids by reverse osmosis prevents thermal breakdown of the long chain glucomannons and polyphenols, maximizing the efficaciousness of the finished product.

In another embodiment, the method includes adjusting the pH of the concentrated juice and soluble solids to substantially match the pH of coffee. Preferably, the concentrate is adjusted to a pH of about 5.0. The method can also include subjecting the adjusted concentrate to a second pasteurization step. Preferably, the second pasteurization step is also carried out by flash pasteurizing the concentrate at a temperature of at least about 170° F., more preferably at least about 180° F., and most preferably at least about 192° F. for about 10 seconds.

In one embodiment, the method also includes filtering the juice and soluble solid fractions to provide a substantially clear liquid. This filtering step is preferably carried out following the initial separation step and prior to the first flash pasteurization step. The filtering step is preferably accomplished by recycling the juice through a diatomaceous earth filter. Such a filtering process is well known and can be accomplished using a plate and frame filter press, in which the diatomaceous earth accounts for about 10 wt % of the filter cake. The substantially clear liquid is preferably pasteurized and concentrated to a concentrate suitable for freeze-drying. The pH of the substantially clear liquid is also preferably adjusted to substantially match the pH of coffee.

It is also contemplated that the method includes adding at least one preservative to the nopal juice and/or soluble solid fractions prior to freeze-drying. While any number of known preservatives can be used, the preferred preservatives are sodium benzoate and potassium sorbate. For example, it has been found that adding 0.05% sodium benzoate and 0.05% potassium sorbate, based on the weight of the total concentrate, maintains the freshness of the concentrate without adversely affecting the taste or appearance of the final product.

The concentrated juice and soluble solids are preferably freeze-dried to form a powder that has a moisture content of less than about 12%, more preferably less than about 10% and most preferably less than about 7% by weight. The freeze-dried powder can be ground to a selected size prior to blending with the ground coffee beans. Preferably, the freeze-dried nopal powder is ground to a size sufficient to permit 100% of the powder to pass through a 100 mesh screen.

The final blend preferably contains about 2 to about 30 wt %, more preferably, about 5 to about 25 wt % and, most preferably, about 5 wt % of the ground freeze-dried nopal powder.

Referring to the drawing, FIG. 1 depicts a flow chart showing the procedure for manufacturing a nopal pad isolate and coffee composition according to a preferred embodiment of the present invention.

Young nopal pads, i.e., new petal growth pads, are selectively harvested from cactus plants of the *opuntia ficus indica* and/or *opuntia streptacantha lemaire* variety prior to flowering by cutting each leaf (or pad) manually (step S100).

The harvested nopal pads are then washed in a water and chlorine mixture to remove organic debris (step S101).

Next, the washed pads are manually de-thorned (step S102).

The de-thorned pads are then soaked in a sodium bicarbonate solution at a pH of about 7.5 for about 10 minutes (step S103).

The de-thorned pads are then roasted in an Excelsior Drum Roaster, at a temperature in the range of about 250° F. to about 398° F. for a total of about 3-5 minutes with each side being roasted for approximately 1.5-2.5 minutes to a medium dark roast (step S104).

The roasted pads are then ground using a hammer mill grinder equipped with steam nozzles to release and dissociate the juice and soluble solid fractions from the insoluble fiber/solid fractions of the pads. Steam is introduced through the steam nozzles to immediately heat the ground nopal material to at least about 160° F., to inactivate the cellulase enzyme that is naturally present in the fresh nopal pads and to reduce the viscosity of the juice/soluble fractions (step S105).

The insoluble pulp is then removed by filtering the juice/soluble fractions using a Brown Model 3900 or 2503 screw type finisher (step S106).

Next, the screened juice/soluble fractions is filtered using a diatomaceous earth (D.E.) filter aide in a plate and frame filter press, in which the D.E. is about 10 wt % of the filter cake and the filtrate is recycled until the filtrate is a clear juice stream (step S107).

The clear juice is then flash pasteurized at temperature of about 192° F. for about 10 seconds (step S108).

Next, water is removed from the juice at room temperature using reverse osmosis to achieve about a 12 to 15 wt % solids concentration (step S109).

Sodium benzoate and/or potassium sorbate are then added as preservatives to the concentrate in amounts to achieve 0.05 wt % sodium benzoate and 0.05 wt % potassium sorbate, based on the total weight of the concentrate (step S 110).

Next, the pH of the concentrate is adjusted to about 5.0 (step S111).

The adjusted concentrate is then flash pasteurized at a temperature of about 192° F. for about 10 seconds (step S112).

The pasteurized concentrate is then freeze-dried to provide a freeze-dried nopal isolate having a moisture content of less than about 7 wt % (step S113).

The freeze-dried nopal isolate is then ground to powder having a particle size in which at least about 100% of the powder passes through a 100 mesh screen (step S114).

The ground powder is then thoroughly blended with roasted ground coffee beans, to provide a blend containing about 5 wt % of the ground freeze-dried nopal powder (step S115).

In another aspect, the invention is more generally directed to a dietary supplement, which includes a nopal cactus isolate derived from the juice and/or soluble solid fractions of nopal pads of the *opuntia ficus indica* and/or *opuntia streptacantha lemaire* variety.

In one embodiment, the supplement includes a therapeutically effective amount of the isolate to reduce or maintain weight, to reduce cholesterol, or to both reduce (or maintain) weight and reduce cholesterol. Preferably, the isolate is substantially free of the insoluble solid and fibrous components naturally present in the nopal pads. Preferably, the nopal pad isolate contains less than about 1 wt %, more preferably less than about 0.5 wt %, and most preferably less than about 0.1 wt % of insoluble fiber or solid components. It is also preferred that the yield of isolate from the initial juice, i.e., the juice produced by grinding and removing the insoluble solid and fibrous fractions, is at least about 1%, more preferably 1.5% and most preferably about 2% of the juice and soluble solid components.

The nopal pad isolate according to the invention is preferably rich in the pectin, nutrients, flavonoids, glucomannons and polyphenols naturally found in the nopal pads. Preferably, the isolate is prepared in a manner which avoids significant cleavage or breakdown of the long chain glucomannons and polyphenols found in the juice and soluble solid fractions of the nopal pads.

The isolate is preferably derived from young nopal pads harvested prior to flowering of the plant. Preferably, the nopal pads are roasted in a controlled manner prior to juicing to enhance the flavor of the isolate.

It is contemplated that the isolate can be added to any suitable carrier or edible additive. In one embodiment, the supplement is in liquid form with the isolate being added to any of a variety of water-based foodstuffs, such as drinks, for example, juice drinks, sports drinks or drink mixes. Preferably, the supplement is in the form of a hot beverage, for example, a brewed or instant tea or coffee. The brewed tea or coffee can be produced by brewing a composition containing tea leaves and the nopal isolate or a composition containing ground coffee and the nopal isolate, respectively. The instant tea or coffee can be produced by freeze-drying or otherwise forming the brewed tea or coffee into a reconstitutable powder that can be reconstituted with hot water. Alternatively, a standard instant tea or coffee can be blended with a reconstitutable nopal isolate powder. Preferably, the supplement is in a form selected from the group consisting of a juice, coffee and tea.

In yet another aspect, the invention is directed to a method for making a dietary supplement, which includes roasting nopal cactus pads of the *opuntia ficus indica* and/or *opuntia streptacantha lemaire* cactus variety; grinding the roasted pads; substantially separating juice and soluble solid fractions from insoluble fractions of the ground and roasted pads; and freeze-drying the juice and soluble fractions to form a powder.

The method can include blending the powder with ground roasted coffee beans to provide a composition suitable for brewing coffee. In such a case, the roasting step is preformed under conditions to make the taste compatible with brewed coffee.

The method can also include, prior to freeze-drying, the steps of heating the ground nopal pads to inactivate the cellulase enzyme naturally present in fresh nopal pads; filtering out the insoluble pulp from the nopal pad juice and soluble solid fractions; filtering the nopal pad juice and soluble solid fractions until the juice becomes clear; pasteurizing the clear juice; concentrating the pasteurized juice to a concentration suitable for freeze-drying; adjusting the pH of the concentrate; and subjecting the concentrate to a second pasteurization step. Preferably, the pH is adjusted to about 5.0. The method can also include adding at least one preservative to the juice. In one embodiment, the method results in yield of the juice and soluble fractions by weight that is at least 30% or greater, preferably at least 40% or greater, and, more preferably, at least 50% or greater of the total weight of the starting nopal pads. Preferably, the yield of the isolate from the juice and soluble solid fraction is at least about 1% or greater, preferably at least about 1.5% or greater, and more preferably at least about 2% or greater of the total weight of the juice and soluble solids.

In yet another aspect, the invention is directed towards a method for lowering cholesterol, stabilizing blood glucose levels and/or promoting healthy weight management. The method includes administering a nutritional supplement or food stuff which includes a nopal cactus isolate, as described above, to someone in need thereof, in an therapeutically effective amount and at a frequency sufficient to lower cholesterol, stabilize blood glucose and insulin levels and/or promote healthy weight management. Preferably, the nutritional supplement or food stuff in the form of coffee made from the composition for making coffee discussed above.

Preferably, the person in need of lowering cholesterol, stabilizing blood glucose levels or weight reduction (or stabilization) will consume between about 2 and 4 cups of coffee made from the composition, as described above. The effectiveness of the composition in lowering cholesterol, stabilizing blood glucose levels and promoting weight management is generally dependent upon the individuals body weight and physiology. Thus, the amount administered will be dependent upon the individual's needs.

In another aspect, the invention is directed to an item of manufacture which includes a container containing a coffee composition, that includes a blend of ground roasted coffee and a nopal cactus isolate, wherein the container is associated with printed labeling advising of the attributes or benefits of the coffee composition. The attributes or benefits can include lowering cholesterol, stabilizing blood glucose levels or reducing (or maintaining) weight by consuming coffee made from the coffee composition.

EXAMPLES

The following non-limiting examples have been carried out to illustrate preferred embodiments of the invention. These examples include the preparation of a nopal pad isolate, a coffee product, evaluations of the coffee product according to the invention and anticipated benefits of the products according to the invention.

Example 1

The following example relates to a method for preparing a nopal pad isolate according to the invention. Approximately one metric ton (about 2,200 pounds) of young nopal pads of the *opuntia ficus indica* variety were manually harvested. The nopal pads were washed in a water and chlorine mixture to remove organic debris. The nopal pads were then de-thorned manually. The de-thorned pads were then soaked in a sodium bicarbonate solution having a pH of about 7.5 for about 10 minutes.

After soaking, the pads were roasted in an Drum Roaster, Probat Model Excelsior, at a temperature of about 375° F. for about 3 minutes. The roasted pads were inspected to ensure a medium dark roast, i.e., a level 2 roast on the coffee roasting scale.

The roasted nopal pads were ground using a Ritz disintegrator hammer mill grinder, Model No. RP12, equipped with steam muzzles. The nopal material was immediately steam heated to a temperature of about 160° F. by introducing steam through the steam nozzles.

The insoluble pulp was separated from the juice by filtering the juice using a Brown Model No. 3900 screw type finisher. Approximately 130 gallons of juice was obtained. The resulting juice was passed through a plate and frame filter press containing a diatomaceous earth (D.E.) filter aide. The D.E. accounted for about 10 wt % of the filter cake. The juice stream was recycled until the juice coming out was clear.

The clear juice was then flash pasteurized using an APV plate heat exchanger at a temperature of about 192° F. for about 10 seconds. Water was then removed from the clear juice using an Osmonix reverse osmosis system, having a maximum flow rate of about 5 gpm at 700 psi, to achieve about a 12 wt. % solids concentration.

Sodium benzoate and potassium sorbate were added to the concentrate to achieve about 0.05% sodium benzoate and 0.05% potassium sorbate, based on the weight of the concentrate. The pH was then adjusted to about 5 using citric acid. The adjusted concentrate was again flash pasteurized at about 192° F. for about 10 seconds.

The pasteurized concentrate was then freeze dried using a Cuddon FD 80 freeze dryer to produce approximately 22 pounds of a freeze dried powder having a moisture content of about 6 wt %.

The freeze dried nopal isolate powder was then ground using a Fitzmill Model D grinder to a particle size such that essentially 100% of the particles would pass through a 100 mesh screen. Approximately 22 pounds of the nopal isolate powder were obtained.

Example 2

The following example relates to a method for preparing a composition for making coffee according to the invention. Approximately 1,200 grams of roasted coffee beans were ground to a size suitable for making automatic drip coffee. The ground coffee beans were combined with approximately 60 grams of the freeze dried nopal isolate powder from Example 1 and were thoroughly blended using a Ross Ribbon Blender Model 42N.

Example 3

This example relates to a method for preparing coffee according to the invention. Approximately, 75.6 grams of the coffee/nopal isolate blend from Example 2 were placed in a standard coffee filter and brewed into coffee using a Krups automatic drip coffee maker. Approximately 6 cups, containing about 6 oz. per cup, of a coffee beverage were produced.

The resulting coffee was palatable and had an acceptable taste and flavor expected for a coffee drinking experience.

Example 4

Three groups of laboratory rats are each fed with a blend of 0.25% cholesterol and 2 g coffee. In each test group the concentration of nopal isolate in the coffee is varied so that the coffee contains approximately 0%, 3% and 5%, respectively. Serum total cholesterol and lipoprotein profile is determined for each group. After one month feeding, blood is withdrawn and serum total cholesterol, HDL and LDL is determined. Rats receiving a 5% nopal isolate-coffee blend have lower weight gain when compared with counterparts being fed 3% or the control 0%. Consumption of diet with coffee with 0% nopal isolate have essentially no affect on total cholesterol and LDL cholesterol levels, however rats fed with freeze dried nopal isolate at 5% concentration levels have a significant, e.g. 34%, reduction of LDL cholesterol levels. Consumption of nopal isolate has no affect on HDL cholesterol levels. Thus, it can be concluded that the freeze dried nopal isolate has potentially beneficial effect for hypercholesterolemia individuals.

Example 5

The effect of nopal soluble fiber vs. nopal soluble fiber and coffee blend on low density lipoprotein (LDL) metabolism is investigated by feeding 8 men with dyslipidema either a diet containing 5% nopal isolate freeze dried juice concentrate mixed in water with no coffee or 5% nopal isolate freeze dried juice concentrate blended in hot coffee. After 6 weeks, blood is withdrawn and plasma cholesterol profile is analyzed. Cholesterol levels are believed to be significantly decreased by the nopal isolate/coffee blend diet, e.g., a 36% decrease in LDL levels and hepatic free and esterified cholesterol levels reduced 33%. The 5% nopal isolate freeze dried juice concentrate in water with no coffee shows a significantly smaller decrease, e.g., only a 28% decrease in LDL levels and hepatic free and esterified cholesterol levels only reduced by 30%. These data suggest that nopal isolate taken with hot coffee is more effective in lowering cholesterol than nopal isolate with no coffee.

Example 6

Five to fifty men are selected for clinical study. The men are considered obese, i.e., having a Body Mass Index ("BMI") in excess of 30. BMI is calculated by dividing a person's weight (in lbs) by their height (in inches) and multiplying by 704.5. All the men in the study are restricted to a controlled diet, in which the total amount of calories, carbohydrates and fats are approximately the same for each subject. The men are divided into four groups, the first of which receives 2 servings of regular instant coffee per day (with a serving being about 4.5 grams of regular instant coffee mixed with 6 ounces of hot water, the second of which receives 2 servings of the nopal pad isolate per day (with a serving being about 0.5 grams of the isolate mixed with 6 ounces of hot water), the third of which receives 2 servings of nopal isolate enriched coffee (with a serving being about 4.5 grams of instant regular instant coffee and about 0.5 grams of the nopal isolate mixed with 6 ounces of hot water), and the fourth of which receives no supplement (the "control" group). The diets of the groups are selected to include no further source of weight loss or diet supplements. The diets are continued for 6 months.

Prior to beginning the diets, the subjects are weighed. The subjects are weighed again for each group after the groups have been on the respective diets for 6 months. The results are compared between members of each group and between the beginning of the study and end of the study for each member. Enhanced weight loss by the combination of the coffee and nopal isolate is shown by a greater percent decrease weight in the combination group relative to the coffee group, the nopal isolate group, and the control group.

Utility of the combination of the coffee and nopal isolate for weight loss in a human is evidenced by activity in the above example.

Thus, while there has been disclosed what is presently believed to be the preferred embodiments of the invention, those skilled in the art will appreciate that other and further changes and modifications can be made without departing from the scope or spirit of the invention, and it is intended that all such other changes and modifications are included in an are within the scope of the invention as described in the appended claims.

We claim:

1. A health benefit composition for making coffee comprising a nopal cactus isolate derived from nopal pads of *opuntia ficus indica, opuntia streptacantha lemaire* variety and combinations thereof in an amount sufficient to effect an attribute or benefit selected from the group consisting of lowering cholesterol, stabilizing blood glucose levels, stabilizing blood insulin levels, reducing weight, maintaining weight, and combinations thereof, and roasted ground coffee beans; and wherein said nopal cactus isolate is derived from the juice and/or soluble fractions of said nopal pads.

2. A composition according to claim 1, wherein said nopal cactus isolate is freeze-dried.

3. A composition according to claim 2, wherein said freeze-dried isolate is present in an amount sufficient to enhance weight reduction as a result of consuming said coffee.

4. A composition according to claim 2, wherein said freeze-dried isolate is present in an amount sufficient to reduce cholesterol as a result of consuming said coffee.

5. A composition according to claim 2, wherein said nopal pads are young nopal pads harvested prior to flowering of the cactus plant.

6. A composition according to claim 1, wherein said nopal pads are roasted in a controlled manner to enhance the flavor of said isolate.

7. A composition according to claim 6, wherein said isolate has a flavor compatible with brewed coffee.

8. A composition according to claim 1, wherein said composition is in a form suitable for making coffee by a method selected from the group consisting of drip, percolation, press, espresso, latte, instant coffee and flow-through bag.

9. A composition according to claim 8, wherein said coffee is intended to be served hot.

10. A dietary supplement, comprising a nopal cactus isolate derived from the juice and/or soluble solid fractions of nopal pads of the *opuntia ficus indica* and/or *opuntia streptacantha lemaire* variety and roasted ground coffee beans.

11. A dietary supplement according to claim 10, wherein said supplement comprises an effective amount of said isolate to reduce or maintain weight.

12. A dietary supplement according to claim 10, wherein said supplement comprises an effective amount of said isolate to reduce cholesterol.

13. A dietary supplement according to claim 10, wherein said isolate is derived from young nopal pads harvested prior to flowering of the plant.

14. A dietary supplement according to claim 10, wherein said nopal pads are roasted to enhance the flavor of said isolate.

15. An item of manufacture comprising a container containing a coffee composition, said coffee composition comprising a blend of ground roasted coffee beans and a nopal cactus isolate derived from nopal pads of *opuntia ficus indica, opuntia streptacantha lemaire* variety, wherein the container is associated with printed labeling advising of attributes or benefits of the coffee composition selected from the group consisting of lowering cholesterol, stabilizing blood glucose levels, stabilizing blood insulin levels, reducing weight, maintaining weight and combinations thereof; and wherein said nopal cactus isolate is derived from the juice and/or soluble fractions of said nopal pads thereof.

* * * * *

UNITED STATES PATENT AND TRADEMARK OFFICE
CERTIFICATE OF CORRECTION

| | | |
|---|---|---|
| PATENT NO. | : 7,399,490 B2 | |
| APPLICATION NO. | : 10/847217 | |
| DATED | : July 15, 2008 | |
| INVENTOR(S) | : Agarwala et al. | |

It is certified that error appears in the above-identified patent and that said Letters Patent is hereby corrected as shown below:

IN THE SPECIFICATION:

<u>In Column 3, Line 50</u>

Now reads "cleaned and de-thomed"
Should read -- cleaned and de-thorned --

<u>In Column 7, Line 23</u>

Now reads "cleaned and de-thomed"
Should read -- cleaned and de-thorned --

<u>In Column 7, Line 35</u>

Now reads "cleaned and de-thomed"
Should read -- cleaned and de-thorned --

<u>In Column 9, Line 24</u>

Now reads "pads are manually de-thomed"
Should read -- pads are manually de-thorned --

<u>In Column 9, Line 26</u>

Now reads "The de-thomed pads"
Should read -- The de-thorned pads --

UNITED STATES PATENT AND TRADEMARK OFFICE
CERTIFICATE OF CORRECTION

PATENT NO. : 7,399,490 B2
APPLICATION NO. : 10/847217
DATED : July 15, 2008
INVENTOR(S) : Agarwala et al.

It is certified that error appears in the above-identified patent and that said Letters Patent is hereby corrected as shown below:

<u>In Column 9, Line 29</u>

Now reads "The de-thomed pads"
Should read -- The de-thorned pads --

Signed and Sealed this

Twenty-eighth Day of October, 2008

JON W. DUDAS
*Director of the United States Patent and Trademark Office*